(12) United States Patent
Imamura (10) Patent No.: US 11,690,598 B2
(45) Date of Patent: Jul. 4, 2023

(54) ULTRASOUND DIAGNOSTIC APPARATUS AND NON-TRANSITORY STORAGE MEDIUM

(71) Applicant: Canon Medical Systems Corporation, Otawara (JP)

(72) Inventor: Tomohisa Imamura, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 632 days.

(21) Appl. No.: 16/515,229

(22) Filed: Jul. 18, 2019

(65) Prior Publication Data
US 2020/0022679 A1 Jan. 23, 2020

(30) Foreign Application Priority Data

Jul. 20, 2018 (JP) ................................ 2018-137258
Jul. 17, 2019 (JP) ................................ 2019-131939

(51) Int. Cl.
| | |
|---|---|
| A61B 8/08 | (2006.01) |
| H04B 11/00 | (2006.01) |
| G01S 7/52 | (2006.01) |
| A61B 8/00 | (2006.01) |
| G01S 15/89 | (2006.01) |

(52) U.S. Cl.
CPC ............ A61B 8/483 (2013.01); A61B 8/4483 (2013.01); A61B 8/5207 (2013.01); A61B 8/54 (2013.01); G01S 7/5209 (2013.01); G01S 7/52085 (2013.01); G01S 15/8925 (2013.01); H04B 11/00 (2013.01)

(58) Field of Classification Search
CPC ..... A61B 8/483; A61B 8/4483; A61B 8/5207; A61B 8/54; G01S 7/52085; G01S 7/5209; G01S 15/8925; H04B 11/00
See application file for complete search history.

(56) References Cited

U.S. PATENT DOCUMENTS

| | | | |
|---|---|---|---|
| 2004/0064048 A1 | 4/2004 | Li | |
| 2013/0066207 A1* | 3/2013 | Prater | ................ G01S 7/52095 600/440 |

FOREIGN PATENT DOCUMENTS

| | | |
|---|---|---|
| JP | 2004-113794 | 4/2004 |
| JP | 2013-000414 | 1/2013 |

(Continued)

*Primary Examiner* — Keith M Raymond
*Assistant Examiner* — Fikirte (Fiki) T Ashine
(74) *Attorney, Agent, or Firm* — Oblon, McClelland, Maier & Neustadt, L.L.P.

(57) ABSTRACT

According to one embodiment, an ultrasound diagnostic apparatus includes a transmitter/receiver and processing circuitry. The transmitter/receiver sequentially transmits a first transmission beam group and a second transmission beam group and receives at least one reception beam for each transmission beam, via an ultrasound probe having a plurality of transducers arranged along an azimuth direction and an elevation direction. The processing circuitry combines a first reception beam based on a first transmission beam included in the first transmission beam group and a second reception beam based on a second transmission beam included in the second transmission beam group. Transmission beams that are adjacent to each other in the azimuth direction or the elevation direction belong to transmission beam groups that are different from each other.

14 Claims, 4 Drawing Sheets

(56) References Cited

FOREIGN PATENT DOCUMENTS

| | | | | |
|---|---|---|---|---|
| JP | 2013000414 | A | * | 1/2013 |
| JP | 2013-526390 | A | | 6/2013 |
| JP | 2014-207990 | | | 11/2014 |
| JP | 2014207990 | A | * | 11/2014 |
| JP | 2017-136251 | A | | 8/2017 |
| JP | 2018-064852 | A | | 4/2018 |

* cited by examiner

ULTRASOUND DIAGNOSTIC APPARATUS AND NON-TRANSITORY STORAGE MEDIUM

CROSS-REFERENCE TO RELATED APPLICATIONS

This application is based upon and claims the benefit of priority from the prior Japanese Patent Applications No. 2018-137258, filed Jul. 20, 2018 and No. 2019-131939, filed Jul. 17, 2019, the entire contents of both of which are incorporated herein by reference.

FIELD

Embodiments described herein relate generally to an ultrasound diagnostic apparatus and a non-transitory storage medium.

BACKGROUND

Ultrasound diagnostic apparatuses of a two-dimensional array probe type, in which a plurality of ultrasound transducers are arranged in the form of a matrix, have been developed. An ultrasound diagnostic apparatus having a two-dimensional array probe realizes parallel signal processing so that reflected wave signals generated on multiple scanning lines can be simultaneously received in response to a single ultrasound transmission.

The ultrasound diagnostic apparatus may form a transmission beam having a relatively wide range of acoustic field, and simultaneously form reception beams having a relatively narrow range of acoustic field at different positions. The ultrasound diagnostic apparatus generates an image by repeating formation of transmission beams and formation of reception beams at positions shifted from each other in the imaging target space. In this image generation, streaks may appear on the generated image in the beam formation direction (scanning line direction). To make such streaks unnoticeable, images may be subjected to a post-processing treatment of smoothing. However, this treatment tends to trigger another problem that is degradation of the spatial resolution.

DETAILED DESCRIPTION

In general, according to one embodiment, an ultrasound diagnostic apparatus includes a transmitter/receiver and processing circuitry. The transmitter/receiver sequentially transmits a first transmission beam group and a second transmission beam group and receives at least one reception beam for each transmission beam, via an ultrasound probe having a plurality of transducers arranged along an azimuth direction and an elevation direction. The processing circuitry combines a first reception beam based on a first transmission beam included in the first transmission beam group and a second reception beam based on a second transmission beam included in the second transmission beam group. Transmission beams that are adjacent to each other in the azimuth direction or the elevation direction belong to transmission beam groups that are different from each other.

The present embodiment will be explained below, by referring to the drawings.

Figure 1:
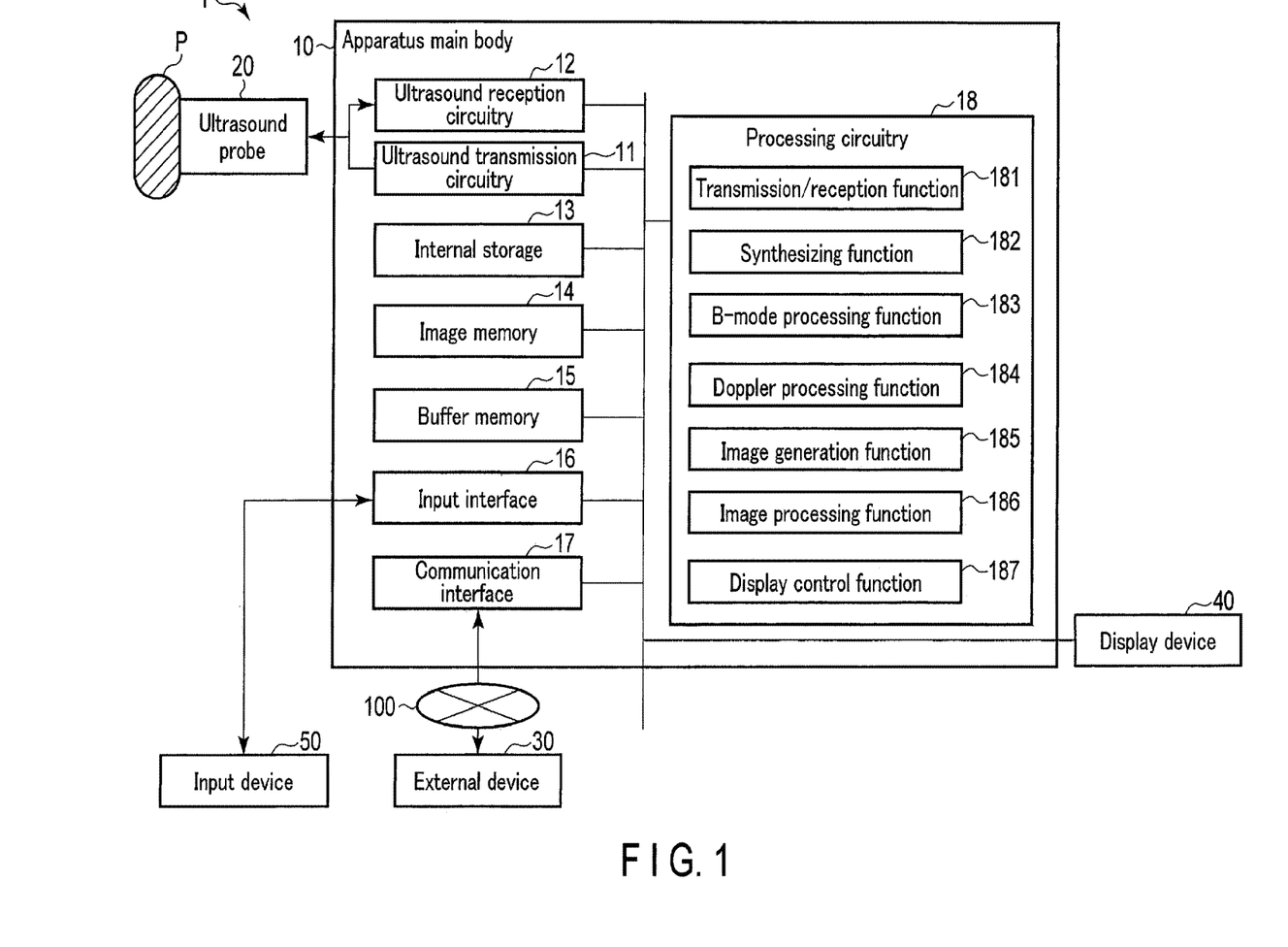
FIG. 1 is a block diagram showing the structure of an ultrasound diagnostic apparatus according to the present embodiment.

FIG. 1 is a block diagram showing an exemplary structure of an ultrasound diagnostic apparatus 1 according to the present embodiment. As illustrated in FIG. 1, the ultrasound diagnostic apparatus 1 includes an apparatus main body 10 and an ultrasound probe 20. The apparatus main body 10 is connected to an external device 30 via a network 100. The apparatus main body 10 is also connected to a display device 40 and an input device 50.

The ultrasound probe 20 executes ultrasound scanning in a scan area of a subject P under the control of, for example, the apparatus main body 10. The ultrasound probe 20 includes a plurality of ultrasound transducers, a matching layer on the ultrasound transducers, and a backing material that prevents the ultrasound waves from propagating backward from the ultrasound transducers. The ultrasound probe 20 according to the present embodiment is a two-dimensional array probe, in which a plurality of ultrasound transducers are arranged in the form of a matrix. Specifically, the ultrasound probe 20 includes ultrasound transducers arranged in multiple columns in the azimuth direction and in multiple rows in the elevation direction. The ultrasound probe 20 is detachably coupled to the apparatus main body 10.

The piezoelectric oscillators generate ultrasound waves in response to drive signals supplied from an ultrasound transmission circuitry 11 included in the apparatus main body 10. Ultrasound waves are thereby transmitted from the ultrasound probe 20 to the subject P. When ultrasound waves are transmitted from the ultrasound probe 20 to the subject P, the transmitted ultrasound waves are sequentially reflected on the acoustic impedance discontinuous surface of the body tissue of the subject P, and are received as reflected wave signals by piezoelectric transducers of the ultrasound probe 20. The amplitude of a received reflected wave signal depends on the difference in acoustic impedance on the discontinuous surface from which the ultrasound wave is reflected. If the transmitted ultrasound pulse is reflected from the surface of, for example, a moving bloodstream or cardiac wall, the frequency of the resultant reflected wave signal will be shifted due to the Doppler effect, with the shift depending on the velocity component in the ultrasound transmission direction of the moving object. The ultrasound probe 20 receives the reflected wave signal from the subject P, and converts it into an electric signal.

The apparatus main body 10 of FIG. 1 generates an ultrasound image based on the reflected wave signal received by the ultrasound probe 20. The apparatus main body 10 includes ultrasound transmission circuitry 11, ultrasound reception circuitry 12, internal storage 13, an image memory 14 (cine memory), a buffer memory 15, an input interface 16, a communication interface 17, and processing circuitry 18, as illustrated in FIG. 1.

The ultrasound transmission circuitry 11 is a processor that supplies a drive signal to the ultrasound probe 20. The ultrasound transmission circuitry 11 is realized, for example, by trigger generation circuitry, delay circuitry, and pulser circuitry. The trigger generation circuitry repeatedly generates a rate pulse for generating transmission ultrasound waves at a rate frequency predefined by the processing circuitry 18. The delay circuitry gives a delay time for each piezoelectric transducer to each rate pulse generated by the trigger generation circuitry. This delay time is required to converge the ultrasound wave generated from the ultrasound probe 20 into a beam and determine its transmission directivity. The delay time may be determined by the processing circuitry 18. The pulser circuitry applies a drive signal (drive pulse) to the multiple ultrasound transducers of the ultrasound probe 20 at the timing based on a rate pulse. The delay circuitry changes the delay times that are to be given to the rate pulses so that the transmission direction from the surface of the piezoelectric transduces can be adjusted as needed.

The ultrasound reception circuitry 12 is a processor that performs various processes on the reflected wave signals received by the ultrasound probe 20 and thereby generates reception signals. The ultrasound reception circuitry 12 may be realized by amplification circuitry, an A/D converter, reception delay circuitry, and an adder. The amplification circuitry performs gain correction processing by amplifying a reflected wave signal received by the ultrasound probe 20 for each channel. The A/D converter converts the gain-corrected reflected wave signal into a digital signal. The reception delay circuitry provides the digital signal with a delay time required to determine the reception directivity. The delay time may be determined by the processing circuitry 18. The adder sums up a plurality of digital signals to which a delay time is individually given. With the addition processing by the adder, a reception signal, in which a reflection component from a direction corresponding to the reception directivity is emphasized, is generated. The ultrasound transmission circuitry 11 and ultrasound reception circuitry 12 are an example of a transmitter/receiver. The ultrasound transmission circuitry 11 and ultrasound reception circuitry 12 may share at least part of them in common. If software beam forming is adopted by using reflected wave signals, at least part of the function of the ultrasound reception circuitry 12 (e.g., reception beam forming function) may be realized by the processing circuitry 18 instead, which will be described later. That is, the processing circuitry 18 may be an example of the transmitter/receiver.

At least part of the ultrasound transmission circuitry 11 and the ultrasound reception circuitry 12 may be provided in the ultrasound probe 20.

The internal storage 13 includes, for example, a magnetic or optical storage medium, or a processor-readable storage medium such as a semiconductor memory. The internal storage 13 stores therein a program or the like for realizing ultrasound transmission/reception. The internal storage 13 further stores therein data items such as diagnostic information (including patient IDs and medical opinions), diagnostic protocols, transmission conditions, reception conditions, signal processing conditions, image generation conditions, image processing conditions, a body mark generation program, display conditions, and a conversion table for presetting the range of visualization color data for respective diagnostic sites. The above program and data items may be pre-stored in the internal storage 13, or may be stored and distributed in a non-transitory storage medium, read from the non-transitory storage medium and installed in the internal storage 13.

The internal storage 13 may be a driving device that reads and writes various types of information with respect to a portable storage medium such as a CD-ROM drive, DVD drive, or flash memory. The internal storage 13 may also be designed to write the stored data onto a portable storage medium and store the data into an external device 30 by way of a portable storage medium.

The image memory 14 includes, for example, a magnetic or optical storage medium, or a processor-readable storage medium such as a semiconductor memory. The image memory 14 stores therein image data corresponding to a plurality of frames immediately before a freeze operation that is input via the input interface 16. The image data stored in the image memory 14 may be sequentially displayed (as moving images).

The buffer memory 15 includes, for example, a magnetic or optical storage medium, or a processor-readable storage medium such as a semiconductor memory. The buffer memory 15 may be realized by a ring buffer that stores data by overwriting existing data within a predetermined capacity. For example, when a reception signal is input, which exceeds the predetermined capacity, older data in the buffer memory 15 is overwritten. The buffer memory 15 outputs the stored reception signal in response to a command from the processing circuitry 18.

The internal storage 13, image memory 14, and buffer memory 15 do not always have to be realized by independent storage devices. The internal storage 13, image memory 14, and buffer memory 15 may be realized by a single storage device. Each of the internal storage 13, image memory 14, and buffer memory 15 may be realized by multiple storage devices.

The input interface 16 receives various commands from the operator through the input device 50. The input device 50 may include a mouse, a keyboard, panel switches, slider switches, a trackball, a rotary encoder, an operation panel, a touch command screen (TCS), and the like. The input interface 16 is coupled to the processing circuitry 18 via a bus, for example, thereby converting an operation command that is input by the operator, to an electric signal, and outputting this electric signal to the processing circuitry 18. According to the present embodiment, the input interface 16 is not limited to a component that is coupled to a physical operation component such as a mouse and keyboard. Examples of the input interface 16 may include circuitry that is configured to receive an electric signal corresponding to an operation command input from an external input device that is provided separately from the ultrasound diagnostic apparatus 1 and to output this electric signal to the processing circuitry 18.

The communication interface 17 is coupled to an external device 30 via the network 100 or the like, and performs data communications with the external device 30. The external device 30 may be a database such as a picture archiving and communication system (PACS), which is a system that manages data of various medical images, or an electronic medical chart system that manages medical-image attached electronic charts. Any communication standard may be adopted for communications with the external device 30, examples of which include digital imaging and communication in medicine (DICOM).

The processing circuitry 18 may be a processor that functions as the center of the ultrasound diagnostic apparatus 1. The processing circuitry 18 implements the program stored in the internal storage 13, thereby realizing the functions corresponding to the program. The processing circuitry 18 may include a transmission/reception function 181, combining function 182, B-mode processing function 183, Doppler processing function 184, image generation function 185, image processing function 186, and display control function 187.

The transmission/reception function 181 is to control the ultrasound transmission circuitry 11 and the ultrasound reception circuitry 12 to enable the ultrasound probe 20 to perform ultrasound scanning. With the transmission/reception function 181, the processing circuitry 18 controls the transmission of ultrasound waves by the ultrasound transmission circuitry 11 and the reception of reflected wave signals by the ultrasound reception circuitry 12, in accordance with the program read from the internal storage 13.

Specifically, the processing circuitry 18 controls the ultrasound transmission circuitry 11 so that the ultrasound transmission circuitry 11 can apply, to the ultrasound transducers, drive signals to which respective delay times are given. Each of the ultrasound transducers transmits ultrasound waves at a timing based on the given delay time. The ultrasound waves transmitted from the ultrasound transducers are combined into a transmission beam so that the ultrasound waves can be transmitted in a preset direction.

The processing circuitry 18 controls ultrasound transmission/reception so that, as a result of the ultrasound scanning, a plurality of transmission beams can be formed in a predetermined pattern in an ultrasound scanning area (scan area) targeted for image generation.

Figure 2:
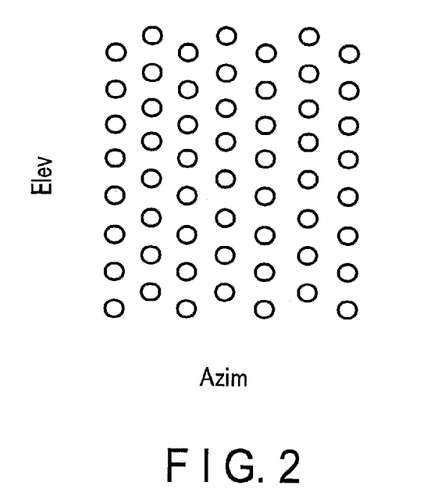
FIG. 2 is a diagram explaining an exemplary spatial arrangement of transmission beams in a scan area in the ultrasound diagnostic apparatus illustrated in FIG. 1.

FIG. 2 is a diagram explaining an exemplary spatial arrangement of transmission beams formed in the scan area as a result of the ultrasound diagnostic apparatus 1 of FIG. 1 performing the ultrasound scanning. For example, a cross section of the transmission beams perpendicular to the central axis of the ultrasound probe and intersecting the beams is schematically shown. In FIG. 2, circles represent the transmission beam formation positions.

As illustrated in FIG. 2, the transmission beam formation positions are arranged along the elevation direction and azimuth direction, in intervals by a certain rule in the scan area. For example, the transmission beam formation positions may be arranged at certain intervals on lines that are parallel in the elevation direction and are aligned at equal intervals in the azimuth direction. Furthermore, the transmission beam formation positions on any two adjacent lines in the azimuth direction may be shifted from each other, for half a distance (half an arrangement interval) of two transmission beams in the elevation direction. In the example of FIG. 2, the transmission beams are shifted to a 0.5 interval. According to the present embodiment, such an arrangement of the transmission beam formation positions will be referred to as "staggered arrangement in the azimuth direction", and the arrangement of the positions of the transmission beams staggered for half an arrangement interval will be referred to as "0.5-beam shifted arrangement".

In the example of FIG. 2, the positions of the transmission beams are linearly arranged in the elevation direction, and staggered in the azimuth direction. The example, however, is not a limitation. In the example of FIG. 2, the arrangement may be symmetric with respect to the elevation direction and azimuth direction. In other words, the transmission beam formation positions may be arranged at certain intervals on lines that are parallel in the azimuth direction and are aligned at equal intervals in the elevation direction. Then, transmission beams on any two adjacent lines in the elevation direction may be shifted from each other, for half a distance (half an arrangement interval) of two transmission beams in the azimuth direction. According to the present embodiment, such an arrangement of transmission beams will be referred to as "staggered arrangement in the elevation direction".

The transmission beams formed by the ultrasound transmission circuitry 11 are sorted into at least three groups in accordance with the distribution of the transmission direction. In other words, the formed transmission beams will belong to one of at least three transmission beam groups. It is preferable that one transmission beam does not belong to two or more different transmission beam groups, and that transmission beams of the same transmission beam group are not positioned adjacent to each other in the azimuth direction or elevation direction.

Figure 3:
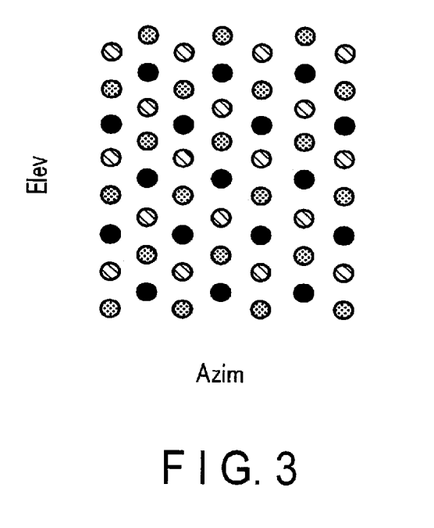
FIG. 3 is a diagram showing the distribution of transmission beam groups formed by the ultrasound transmission circuitry of FIG. 1.

FIG. 3 is a schematic diagram showing an exemplary distribution of transmission beam groups defined by the processing circuitry 18 of FIG. 1. Dotted circles in FIG. 3 represent transmission beams of the first transmission beam group. Shaded circles represent transmission beams of the second transmission beam group. Black circles represent transmission beams of the third transmission beam group. The transmission beams formed in the elevation direction in FIG. 3 are arranged in the order of the transmission beams of the first transmission beam group, the transmission beams of the second transmission beam group, and the transmission beams of the third transmission beam group, along the forward direction of the elevation (i.e., from the bottom to the top of the sheet of FIG. 3). Furthermore, the transmission beams of the same transmission beam group in any two adjacent rows in the azimuth direction are shifted relatively from each other in the elevation direction for a distance corresponding to 1.5 beams. For example, the position of transmission beam A of the first transmission beam group in the first row with respect to the elevation direction is shifted for a distance corresponding to 1.5 beams with respect to transmission beam B, which is the closest one in the elevation direction of the transmission beams of the first transmission beam group on the second row, which is adjacent to the first row. With the transmission beams of the same transmission beam group arranged in the above manner, transmission beams that are adjacent to each other in the azimuth direction or elevation direction will be of different transmission beam groups. In a manner similar to FIG. 2, FIG. 3 illustrates a distribution of transmission beams in two-dimensional space. Each of the transmission beams, however, has a depth, forming a three-dimensional structure. It therefore can be said that FIG. 3 presents a distribution of the first to third transmission beam groups in a three-dimensional space.

The processing circuitry 18 further controls the ultrasound transmission/reception so that a plurality of transmission beams can be formed in a predetermined order in the scan area of FIG. 2. Here, the processing circuitry 18 controls the ultrasound transmission/reception so that a predetermined multiple number of transmission beam groups, for example, three transmission beam groups, can be switched around from group to group and that this switching can be repeated in a predetermined order. In this manner, multiple transmission beams can be formed in the scan area in a predetermined order according to the arrangement rule of FIG. 2, as the transmission beam groups are being cyclically switched. It is preferable that no adjacent transmission beams be formed in succession.

Figure 4:
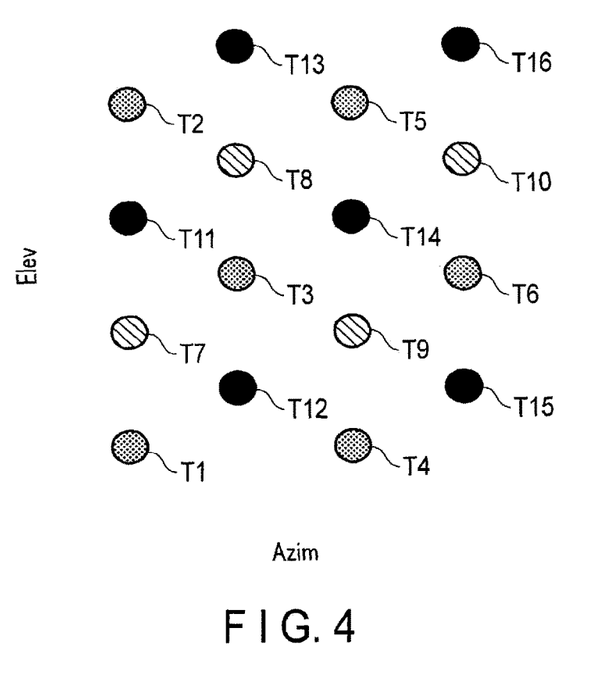
FIG. 4 is a diagram showing the forming order of transmission beams by the ultrasound transmission circuitry of FIG. 1.

FIG. 4 is a schematic diagram showing an exemplary order of the ultrasound transmission circuitry 11 of FIG. 1 forming transmission beams. In this example, 16 transmission beams are to be formed in the scan area. In FIG. 4, the transmission beams are formed, starting from transmission beam T1, which belongs to the dotted first transmission beam group. After the transmission beam T1 is formed, the beam formation position is moved in the elevation direction, where transmission beam T2 is formed. After the transmission beam T2 is formed, the beam formation position is moved in the elevation direction and azimuth direction, where transmission beam T3 is formed. After the transmission beam T3 is formed, the beam formation position is further moved in the elevation direction and azimuth direction, where transmission beam T4 is formed. After the transmission beam T4 is formed, the beam formation position is moved in the elevation direction, where transmission beam T5 is formed. After the transmission beam T5 is formed, the beam formation position is moved in the elevation direction and azimuth direction, where transmission beam T6 is formed.

When the formation of the transmission beams T1 to T6 of the first transmission beam group is completed, the formation of the transmission beams of the shaded second transmission beam group is started, forming transmission beams T7 to T10 of the second transmission beam group in this order. When the formation of the transmission beams T7 to T10 of the second transmission beam group is completed, the formation of the transmission beams of the black-circled third transmission beam group is started, forming transmission beams T11 to T16 of the third transmission beam group in this order. When the formation of the transmission beams T11 to T16 of the third transmission beam group is completed, the formation of transmission beams of a fourth transmission beam group, which is not shown in FIG. 4 and is of the same type as the first transmission beam group, is started.

The beam formation position for each of the first to third transmission beam groups in FIG. 4 is moved at least once in the elevation direction from the initial position, then once in the azimuth direction, and the moving operation is repeated. With regard to the formation order of adjacent transmission beams, the surrounding transmission beams of, for example, the transmission beam T3 are transmission beams T7, T8, T9, T11, T12, and T14. This means that the transmission beams are suitably distributed in a well-balanced order.

The direction of the movement of the beam formation position is not limited to the elevation direction and thereafter in the azimuth direction. When the transmission beams are to be formed linearly along the azimuth direction so as to be staggered in the elevation direction, the beam formation position may be moved at least once in the azimuth direction, then once in the elevation direction, and the moving operation may be repeated.

Furthermore, the processing circuitry 18 may generate at least one reception signal by providing each of the reflected wave signals received by the ultrasound probe 20 with a delay time in consideration of the reception directivity, and summing up the delay-time added reflected wave signals. In this manner, at least one reception beam is formed with respect to a single transmission beam. The number of reception beams formed with respect to one transmission beam is not limited to one, and may be more than one.

The ultrasound reception circuitry 12 generates at least one reception signal, based on each of the reflected wave signals of the ultrasound waves transmitted in multiple directions. In other words, at least one reception beam is formed in response to each transmission beam. According to the present embodiment, it is assumed that a reception beam is formed at the same position as a transmission beam. However, the formation position of the reception beam does not have to match the formation position of the transmission beam. The formation positions of reception beams generated based on different transmission beams may be the same.

The processing circuitry 18 stores in the buffer memory 15 the generated reception signals, in association with the positions of the reception beams, and transmission beam groups to which the transmission beams belong.

The combining function 182 is to combine the reception signals generated by the ultrasound reception circuitry 12, and this function is part of a combining unit. With the combining function 182, the processing circuitry 18 combines reception beams (reception signals) stored in the buffer memory 15 and corresponding to a transmission beam included in each of the transmission beam groups.

Specifically, when a third reception signal group is generated by the ultrasound reception circuitry 12, the processing circuitry 18 implements the combining function 182. With the implementation of the combining function 182, the processing circuitry 18 combines the reception signals of the three reception beam groups, thereby generating reception data. For example, when the generation of the third reception signals is completed, the processing circuitry 18 may read the first reception signals, second reception signals, and third reception signals from the buffer memory 15. Here, the first reception signals represent the first reception beams that correspond to the first transmission beams of the first transmission beam group. The second reception signals represent the second reception beams that correspond to the second transmission beams of the second transmission beam group. The third reception signals represent the third reception beams that correspond to the third transmission beams of the third transmission beam group. When acquiring the first to third reception signals, the processing circuitry 18 may combine the first to third reception signals into a new reception signal.

After generating the third reception signals, the ultrasound reception circuitry 12 generates the fourth reception signals. The fourth reception signals represent the fourth reception beams that correspond to the fourth transmission beams of the fourth transmission beam group, which is of the same type as the first transmission beam group. When the generation of the fourth reception signals is completed, the processing circuitry 18 may read the second reception signals, third reception signals and fourth reception signals from the buffer memory 15. When acquiring the second to fourth reception signals, the processing circuitry 18 generates a new reception signal based on the second to fourth reception signals, in the same manner as the first to third reception signals combined.

The B-mode processing function 183 is to generate three-dimensional B-mode data based on the reception signal generated by the combining function 182. With the B-mode processing function 183, the processing circuitry 18 generates three-dimensional B-mode data, based on the reception signal generated by the combining function 182 and the reception signals read from the buffer memory 15. With the B-mode processing function 183, the processing circuitry 18 may execute an envelope detection process, logarithmic amplification process, and the like on the reception signals, and thereby generate data (B-mode data) that expresses the signal intensity with luminance. The generated B-mode data is stored in a raw data memory (not shown) as B-mode raw data on a three-dimensional ultrasound scanning line.

The Doppler processing function 184 is to generate data (Doppler data) by analyzing the frequencies of the reception signal generated by the combining function 182 and extracting the motion information of a moving object in the region of interest (ROI) that is set in the scan area, based on the Doppler effect. Specifically, with the Doppler processing function 184, the processing circuitry 18 may generate Doppler data as the motion information of the moving object by estimating the average velocity, average dispersion value, average power value, etc from sampled values at sampling positions. A moving object may be a bloodstream, cardiac tissue, or contrast agent. According to the present embodiment, the processing circuitry 18 generates Doppler data as the motion information of the bloodstream (bloodstream information) by estimating the average bloodstream velocity, average bloodstream dispersion value, average bloodstream power value, etc. from sampled values at sampling positions. The generated Doppler data is stored in a raw data memory (not shown) as Doppler raw data on a three-dimensional ultrasound scanning line.

The processing circuitry 18 may calculate bloodstream information by color Doppler. In color Doppler, the transmission and reception of ultrasonic waves are performed on the same scanning line multiple times. The processing circuitry 18 suppresses signals (clutter signals) related to any stationary tissue or slow-moving tissue by setting a moving target indicator (MTI) filter with respect to data strings of the same position so that bloodstream-related signals can be extracted. The MTI filter may be set before or after combining the reception signals by the combining function 182. The processing circuitry 18 thereby estimates the bloodstream information including the bloodstream velocity, average bloodstream dispersion, and average bloodstream power from the extracted bloodstream signals.

The image generation function 185 is to generate image data based on the data generated by the B-mode processing function 183 and Doppler processing function 184. This function is part of an image generator. For example, with the image generation function 185, the processing circuitry 18 executes, on the B-mode raw data stored in the raw data memory, a raw-voxel conversion, which includes interpolation processing that takes the information of the spatial positions into account. The processing circuitry 18 thereby generates three-dimensional B-mode image data constituted by multiple voxels.

The processing circuitry 18 may also execute a raw-voxel conversion on the Doppler raw data stored in the raw data memory, and generate three-dimensional Doppler image data that visualizes the bloodstream information. The three-dimensional Doppler image data includes velocity image data, dispersion image data, power image data, or any combination of such image data. According to the present embodiment, three-dimensional B-mode image data and three-dimensional Doppler image data may represent volume data. One-line data of the volume data evenly includes information from multiple transmission beam groups.

The image processing function 186 is to execute predetermined image processing on the three-dimensional B-mode image data and three-dimensional Doppler image data.

Specifically, with the image processing function 186, the processing circuitry 18 may execute rendering processing to two-dimensionally display the three-dimensional B-mode image data and three-dimensional Doppler image data on the display device 40. The rendering processing may include volume rendering, surface rendering, and multi-planar reconstruction (MPR). The processing circuitry 18 may further execute image processing (smoothing) for re-generating a brightness average value image, employing multiple image frames of the three-dimensional B-mode image data or three-dimensional Doppler image data. The processing circuitry 18 may execute image processing (edge enhancement) employing a differentiation filter within an image.

The display control function 187 is to control the display, on the display device 40, of the three-dimensional B-mode image data and three-dimensional Doppler image data generated and processed according to the image processing function 186. With the display control function 187, the processing circuitry 18 may execute various types of processing relating to the dynamic range, luminance (brightness), contrast, y curve corrections, and RGB conversion on the three-dimensional B-mode image data or three-dimensional Doppler image data, thereby converting the image data to video signals. The processing circuitry 18 displays a video signal on the display device 40. The processing circuitry 18 may generate a graphical user interface (GUI) to allow the operator to input various commands through the input device 50, and display the GUI on the display device 40. Examples of the display device 40 include a CRT display, a liquid crystal display, an organic EL display, an LED display, a plasma display, or any other display known in the relevant technical field.

As described above, the ultrasound probe 20 according to the present embodiment includes multiple transducers aligned in the azimuth direction and elevation direction. The ultrasound transmission circuitry 11 of the ultrasound diagnostic apparatus 1 transmits ultrasound waves from the ultrasound probe 20 in a manner that multiple transmission beams of the first transmission beam group, of the second transmission beam group, and of the third transmission beam group are evenly distributed, with any transmission beams adjacent to each other in the azimuth direction or elevation direction belonging to different transmission beam groups. The ultrasound reception circuitry 12 forms at least one reception beam in response to every transmission beam. Then, with the combining function 182, the processing circuitry 18 combines the first reception beams based on the first transmission beams of the first transmission beam group, the second reception beams based on the second transmission beams of the second transmission beam group, and the third reception beams based on the third transmission beams of the third transmission beam group. As a result, streaks that tend to appear due to skewed beams among the transmission beams or time differences in the formation of the transmission beams can be suppressed in the volume data.

In addition, the ultrasound transmission circuitry 11 of the ultrasound diagnostic apparatus 1 according to the present embodiment forms the transmission beams of the transmission beam groups in a manner that the beam formation positions of these groups will create a staggered pattern with respect to the azimuth direction or elevation direction. In this manner, streaks can be further effectively suppressed in the volume data.

Moreover, the ultrasound diagnostic apparatus 1 according to the present embodiment includes a buffer memory 15 so that reception signals based on at least three different transmission beam groups can be stored in the buffer memory 15. After combining the reception signals based on the three transmission beam groups, the processing circuitry 18 can hold reception signals based on two out of the three transmission beam groups, at least until a reception signal of the next transmission beam group is generated and the next combining process is executed.

With the transmission/reception function 181, the processing circuitry 18 according to the present embodiment forms the fourth transmission beam group having the same distribution of transmission beams as the first transmission beam group, after forming the transmission beams of the third transmission beam group. Thereafter, with the combining function 182, the processing circuitry 18 combines the second reception beams, the third reception beams, and the fourth reception beams based on the fourth transmission beams of the fourth transmission beam group.

Figure 5:
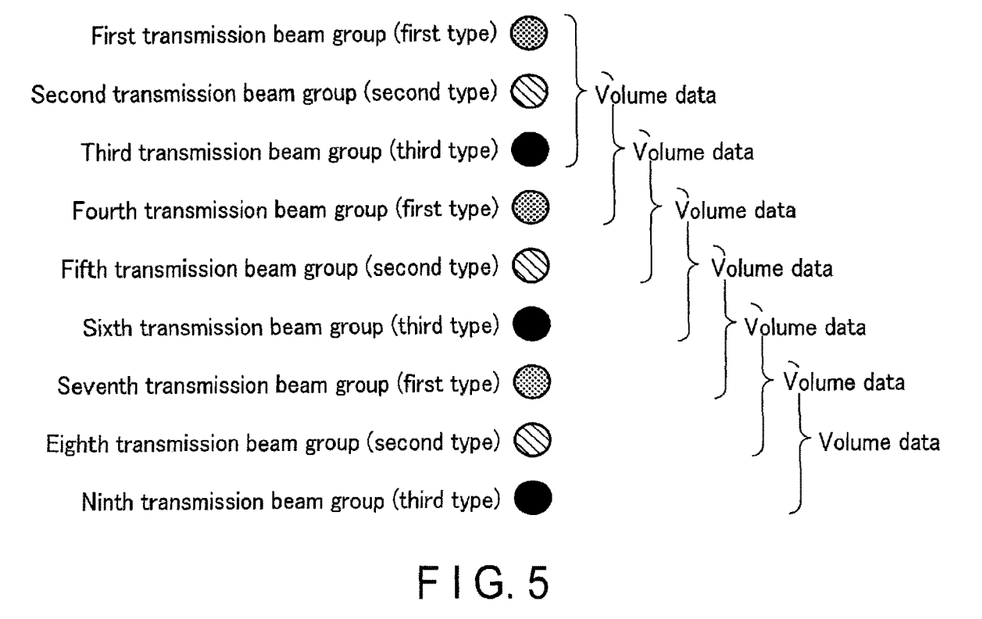
FIG. 5 is a diagram showing the process of generating volume data by the ultrasound diagnostic apparatus of FIG. 1.

FIG. 5 is a schematic diagram showing an exemplary process of generating volume data by the ultrasound diagnostic apparatus 1 of FIG. 1. In this manner, the ultrasound diagnostic apparatus 1 generates new volume data every time reception signals are generated based on a transmission beam group. As a result, the volume rate of the three-dimensional scanning can be enhanced.

With the transmission/reception function 181, the processing circuitry 18 according to the present embodiment forms any adjacent transmission beams in a non-consecutive manner. This temporal symmetry of the transmission beam formation can reduce the influence of the temporal movement, if any, of the examination target, on the volume data.

In the present embodiment, the generation of volume data by the ultrasound diagnostic apparatus 1 has been explained as an example. The data generated by the ultrasound diagnostic apparatus 1, however, is not limited to volume data. The ultrasound diagnostic apparatus 1 may generate two-dimensional data based on the reception signals obtained from the combining process executed by the processing circuitry 18. For example, with the B-mode processing function 183, the processing circuitry 18 may generate two-dimensional B-mode raw data based on the reception beams that are based on transmission beams formed in two columns along the azimuth direction or transmission beams formed in two rows along the elevation direction. The processing circuitry 18 may also generate, with the Doppler processing function 184, two-dimensional Doppler raw data based on reception beams that are based on transmission beams formed in two columns along the azimuth direction or transmission beams formed in two rows along the elevation direction.

In the present embodiment, at least three different groups of transmission beams formed by the ultrasound transmission circuitry 11 have been explained as an example. The transmission beams generated by the ultrasound transmission circuitry 11 may be sorted into two groups. It is preferable that one transmission beam of one transmission beam group does not belong to the other transmission beam group and that transmission beams of the same transmission beam group are not positioned adjacent to each other in the azimuth direction or elevation direction.

Figure 6:
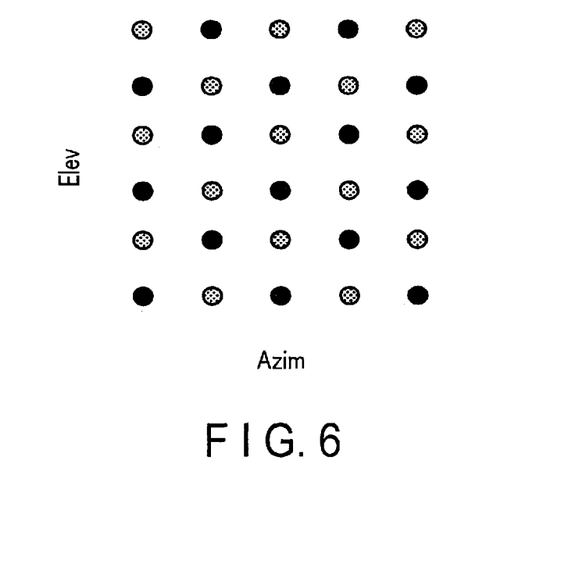
FIG. 6 is a diagram showing another exemplary distribution of transmission beam groups defined by processing circuitry of FIG. 1.

FIG. 6 is a schematic diagram showing another exemplary distribution of transmission beam groups defined by the processing circuitry 18 of FIG. 1. In FIG. 6, dotted circles represent transmission beams of the first transmission beam group. Black circles represent transmission beams of the second transmission beam group. The transmission beams in the elevation direction are arranged along the forward direction of the elevation (i.e., from the bottom to the top of the sheet of FIG. 6) in such a manner that the transmission beams of the first transmission beam group and the transmission beams of the second transmission beam group form an alternating pattern. The transmission beams in the azimuth direction are arranged along the forward direction of the azimuth direction (direction from right to left on the sheet of FIG. 6) in such a manner that the transmission beams of the first transmission beam group and the transmission beams of the second transmission beam group form an alternating pattern. With the transmission beams of the transmission beam groups arranged in the above manner, any transmission beams that are adjacent to each other in the azimuth direction or elevation direction are of different transmission beam groups. FIG. 6 illustrates a distribution of transmission beams in two-dimensional space. Each of the transmission beams, however, has a depth, forming a three-dimensional structure FIG. 6 therefore can be considered as illustrating a distribution of the first and second transmission beam groups in a three-dimensional space.

The processing circuitry 18 further controls the ultrasound transmission/reception so that a plurality of transmission beams can be formed in a predetermined order in a scan area. By this control of the ultrasound transmission/reception, a predetermined multiple number of transmission beam groups, for example, two transmission beam groups, are switched and repeated in a predetermined order. In this manner, the transmission beam groups are cyclically switched so that multiple transmission beams can be formed in the scan area in a predetermined order. It is preferable that no adjacent transmission beams are sequentially formed.

Figure 7:
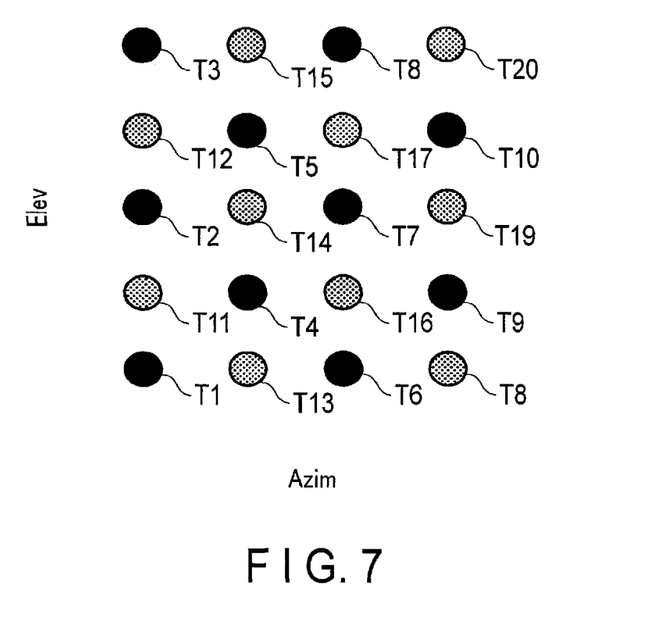
FIG. 7 is a diagram showing another exemplary forming order of transmission beams by the ultrasound transmission circuitry of FIG. 1.

FIG. 7 is a schematic diagram showing another exemplary formation order of transmission beams by the ultrasound transmission circuitry 11 of FIG. 1. In this example, 20 transmission beams are to be formed in the scan area. In FIG. 7, the transmission beams are formed, starting from transmission beam T1, which belongs to the dotted first transmission beam group. After the transmission beam T1 is formed, the beam formation position is moved in the elevation direction and/or azimuth direction, where transmission beams T2 to T10 are sequentially formed.

When the formation of the transmission beams T1 to T10 of the first transmission beam group is completed, the formation of transmission beams of the black-circled second transmission beam group is started, forming transmission beams T11 to T20 of the second transmission beam group in this numbered order. When the formation of the transmission beams T11 to T20 of the second transmission beam group is completed, the formation of transmission beams that belong to the third transmission beam group, which is not shown in FIG. 7 and is the same type as the first transmission beam group, is started.

With the combining function 182, the processing circuitry 18 may combine the reception beams (reception signals) stored in the buffer memory 15 and corresponding to the transmission beams of the different transmission beam groups. Specifically, the processing circuitry 18 implements the combining function 182 when the second reception signals are generated by the ultrasound reception circuitry 12. When the combining function 182 is implemented, the processing circuitry 18 combines two groups of reception signals, thereby generating reception data.

When the second reception signals are generated, the processing circuitry 18 reads the first reception signals and second reception signals from the buffer memory 15. When the first reception signals and second reception signals are read, the processing circuitry 18 combines the first reception signals and second reception signals to generate a new reception signal.

After generating the second reception signals, the ultrasound reception circuitry 12 generates the third reception signals. The third reception signals represent the third reception beams corresponding to the third transmission beams of the third transmission beam group, which is the same type as the first transmission beam group. When the third reception signals are generated, the processing circuitry 18 reads the second reception signals and third reception signals from the buffer memory 15. When the second reception signals and third reception signals are read, the processing circuitry 18 generates a new reception signal based on the second reception signals and third reception signals, in the same manner as the first reception signals and second reception signals combined.

According to the present embodiment explained above, the ultrasound diagnostic apparatus 1 can enhance the accuracy of the volume data generation.

The word "processor" in the embodiment may refer to circuitry such as a central processing unit (CPU), graphics processing unit (GPU), or an application specific integrated circuit (ASIC); or a programmable logic device (e.g., simple programmable logic device (SPLD), complex programmable logic device (CPLD), or field programmable gate array (FPGA)). The processor realizes functions by reading and executing programs stored in the memory circuitry. Instead of storing the programs in the memory circuit, the programs may be directly incorporated in the circuitry of the processor. In this case, the processor realizes the functions by reading and executing the programs incorporated in the circuitry. Each processor of the present embodiment is not limited to a single circuit configured for each processor, but a plurality of independent circuits may be combined into a single processor that can realize the function. Furthermore, the structural components of the embodiment may be integrated into one processor to realize their functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasound diagnostic apparatus, comprising:
a transmitter/receiver configured to sequentially transmit a first group of transmission beams and a second group of transmission beams and receive, as a plurality of reception beams, at least one reception beam for each transmission beam of the first and second groups of transmission beams, via an ultrasound probe having a plurality of transducers arranged along an azimuth direction and an elevation direction; and
processing circuitry configured to combine a first reception beam of the plurality of reception beams based on a first transmission beam included in the first group of transmission beams and a second reception beam of the plurality of reception beams based on a second transmission beam included in the second group of transmission beams,
wherein transmission beams that are adjacent to each other in the azimuth direction or the elevation direction belong to groups of transmission beams that are different from each other,
the transmitter/receiver is further configured to sequentially transmit the first group of transmission beams, the second group of transmission beams, and a third group of transmission beams, and form at least a third reception beam for the third group of transmission beams,
the processing circuitry is further configured to combine the first reception beam, the second reception beam, and the third reception beam,
the transmitter/receiver is further configured to form the first, second, and third groups of transmission beams such that beam formation positions form a staggered pattern along the azimuth direction or the elevation direction,
when forming each group of the first, second, and third groups of transmission beams, the transmitter/receiver is further configured to move a beam formation position, from an initial position, in the elevation direction, and thereafter in the azimuth direction, within the group, and
the processing circuitry is further configured to generate new volume data every time a reception beam is formed for one group of transmission beams.

2. The ultrasound diagnostic apparatus according to claim 1, wherein the transmitter/receiver is further configured to transmit a first transmission beam of the second group of transmission beams sequentially after transmitting a last transmission beam of the first group of transmission beams.

3. The ultrasound diagnostic apparatus according to claim 1, wherein the transmitter/receiver is further configured to transmit a first transmission beam of the second group of transmission beams sequentially after transmitting a last transmission beam of the first group of transmission beams, and further transmit a first transmission beam of the third group of transmission beams sequentially after transmitting a last transmission beam of the second group of transmission beams.

4. The ultrasound diagnostic apparatus according to claim 1, wherein the transmitter/receiver is further configured to form the first reception beam, the second reception beam, and the third reception beam at a same position as corresponding transmission beams of the first, second, and third groups of transmission beams, respectively.

5. The ultrasound diagnostic apparatus according to claim 1, wherein the transmitter/receiver is further configured to form the first reception beam, the second reception beam, and the third reception beam at a position different from corresponding transmission beams of the first, second, and third transmission beams, respectively.

6. The ultrasound diagnostic apparatus according to claim 1, wherein the transmitter/receiver is further configured to form the first reception beam, the second reception beam, and the third reception beam at a same position.

7. The ultrasound diagnostic apparatus according to claim 1, wherein
after forming the second group of transmission beams, the transmitter/receiver is further configured to form the third group of transmission beams having same beam formation positions as the first group of transmission beams, and
the processing circuitry is further configured to combine the second reception beam and a third reception beam based on a transmission beam included in the third group of transmission beams.

8. The ultrasound diagnostic apparatus according to claim 1, wherein
after forming the third group of transmission beams, the transmitter/receiver is further configured to form a fourth transmission beam group having same distribution of transmission beams as the first group of transmission beams, and the processing circuitry is further configured to combine the second reception beam, the third reception beam, and a fourth reception beam based on a fourth transmission beam included in the fourth transmission beam group.

9. The ultrasound diagnostic apparatus according to claim 8, further comprising:
a memory configured to store the first reception beam, the second reception beam, and the third reception beam, and to continue to store at least the second reception beam and the third reception beam after the processing circuitry combines the first reception beam, the second reception beam, and the third reception beam.

10. The ultrasound diagnostic apparatus according to claim 1, further comprising:
an image generator configured to generate a two-dimensional image based on a result of combining the first reception beam, the second reception beam, and the third reception beam.

11. The ultrasound diagnostic apparatus according to claim 1, further comprising:
an image generator configured to generate a three-dimensional image based on a result of combining the first reception beam, the second reception beam, and the third reception beam.

12. The ultrasound diagnostic apparatus according to claim 1, wherein each of the first and second groups of transmission beams are different from each other.

13. A non-transitory storage medium storing a program that, when executed, causes processing circuitry to:
sequentially transmit a first group of transmission beams, a second group of transmission beams and a third group of transmission beams via an ultrasound probe including a plurality of transducers arranged along an azimuth direction and an elevation direction in such a manner that transmission beams adjacent in the azimuth direction or the elevation direction belong to different transmission beam groups;
receive at least one reception beam for each transmission beam; and
combine a first reception beam based on a first transmission beam included in the first group of transmission beams, a second reception beam based on a second transmission beam included in the second group of transmission beams, and a third reception beam based on a third transmission beam included in the third group of transmission beams,
form the first, second, and third groups of transmission beams such that beam formation positions form a staggered pattern along the azimuth direction or the elevation direction,
move a beam formation position, from an initial position, in the elevation direction, and thereafter in the azimuth direction when forming each group of the first, second, and third groups of transmission beams, and
generate new volume data every time a reception beam is formed for one group of transmission beams.

14. An ultrasound diagnostic apparatus, comprising:
a transmitter/receiver configured to sequentially transmit a first group of transmission beams and a second group of transmission beams and receive, as a plurality of reception beams, at least one reception beam for each transmission beam of the first and second groups of transmission beams, via an ultrasound probe having a plurality of transducers arranged along an azimuth direction and an elevation direction;
processing circuitry configured to combine a first reception beam of the plurality of reception beams based on a first transmission beam included in the first group of transmission beams and a second reception beam of the plurality of reception beams based on a second transmission beam included in the second group of transmission beams,
wherein transmission beams that are adjacent to each other in the azimuth direction or the elevation direction belong to groups of transmission beams that are different from each other,
the transmitter/receiver is further configured to sequentially transmit the first group of transmission beams, the second group of transmission beams, and a third group of transmission beams, and forms at least a third reception beam for the third group of transmission beams,
the processing circuitry is further configured to combine the first reception beam, the second reception beam, and the third reception beam,
the transmitter/receiver is further configured to form the first, second, and third groups of transmission beams such that beam formation positions form a staggered pattern along the azimuth direction or the elevation direction,
when forming each group of the first, second, and third groups of transmission beams, the transmitter/receiver is further configured to move a beam formation position, from an initial position, in the azimuth direction, and thereafter in the elevation direction, within the group, and
the processing circuitry is further configured to generate new volume data every time a reception beam is formed for one group of transmission beams.

* * * * *